US005100430A

United States Patent [19]
Avellanet et al.

[11] Patent Number: 5,100,430
[45] Date of Patent: Mar. 31, 1992

[54] BIOPSY FORCEPS DEVICE HAVING A BALL AND SOCKET FLEXIBLE COUPLING

[75] Inventors: Ernesto Avellanet, Miami Lakes; Ernesto Hernandez, Miami, both of Fla.

[73] Assignee: Cordis Corporation, Miami, Fla.

[21] Appl. No.: 576,687

[22] Filed: Aug. 31, 1990

[51] Int. Cl.⁵ .............................................. A61B 10/00
[52] U.S. Cl. .................... 606/205; 606/171; 128/751
[58] Field of Search ............. 128/749, 751, 754; 606/205, 206, 207, 170, 171

[56] References Cited

U.S. PATENT DOCUMENTS

| | | | |
|---|---|---|---|
| 3,964,468 | 6/1976 | Schulz | 606/171 X |
| 4,763,668 | 8/1988 | Macek et al. | 128/751 |
| 4,815,476 | 3/1989 | Clossick | 128/751 |
| 4,950,273 | 8/1990 | Briggs | 606/205 X |

Primary Examiner—Max Hindenburg
Attorney, Agent, or Firm—Tarolli, Sundheim & Covell

[57] ABSTRACT

A biopsy forceps device includes a handle assembly having a handle portion and a hub portion. An elongated flexible hollow body portion preferably in the form of a coiled spring guide wire extends from the hub portion to a forceps assembly. A control wire extends through a lumen in the guide wire as well as a lumen in the hub portion and is coupled at one end to the handle portion and at the other end to the forceps assembly. A flexible coupling interconnects the hub portion with the handle portion so that the hub portion may be angularly displaced with respect to the distal end of the handle portion. The flexible coupling takes the form of a ball and socket arrangement with the ball being carried by the hub portion and the socket being carried by the handle portion.

10 Claims, 1 Drawing Sheet

U.S. Patent     Mar. 31, 1992     5,100,430
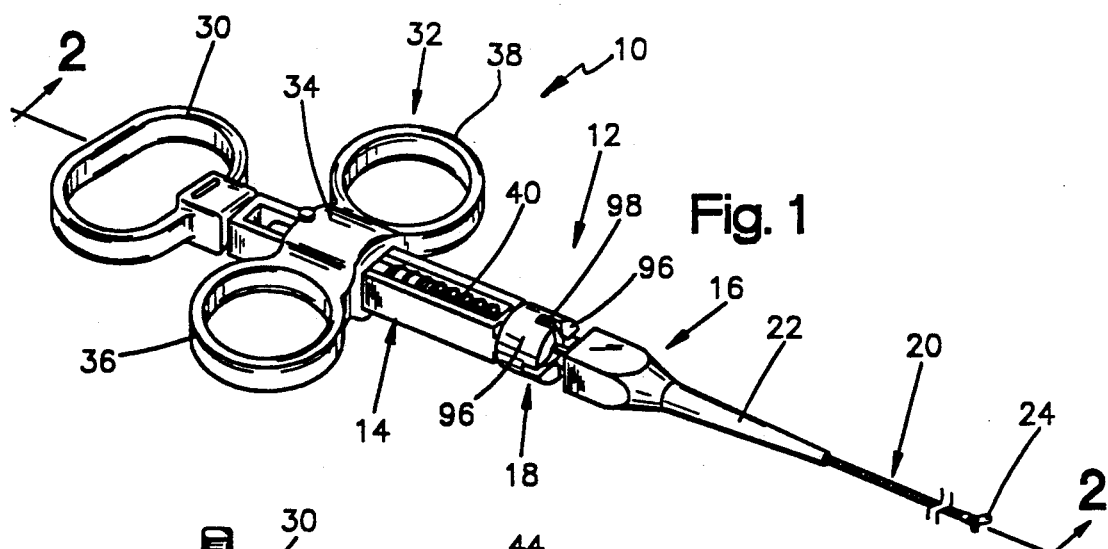

BIOPSY FORCEPS DEVICE HAVING A BALL AND SOCKET FLEXIBLE COUPLING

RELATED APPLICATION

This application is related to our co-pending U.S. patent application Ser. No. 577,919, filed Aug. 31, 1990, pending.

FIELD OF THE INVENTION

The present invention relates to biopsy forceps and more particularly to an improved biopsy forceps having a handle assembly including a ball and socket flexible coupling.

DESCRIPTION OF THE PRIOR ART

Biopsy forceps are known in the art and are in wide use for purposes of obtaining a biopsy sample. One example of the prior art takes the form of the U.S. Pat. No. 4,815,476 to J. P. Clossick assigned to the same assignee as the present invention. Such a forceps device includes a handle assembly slidably mounting a trigger member thereon and an elongated coil spring guide wire connected to the handle assembly at the proximal end of the guide wire. A pair of forceps are mounted to the distal end of the guide wire and a stylet-control wire received within the guide wire is connected at its proximal end to the trigger and its distal end to the pair of forceps.

A guide sheath may be introduced into a patient's body vessel, such as an artery, and the distal end of the forceps device is introduced into the sheath and guided to the site of interest. The handle assembly remains outside of the patient's body allowing the attending physician to operate the trigger. Forward movement of the trigger causes the stylet-control wire to move the forceps to an open position and rearward movement of the trigger causes the pair of forceps to move to a closed position to capture a tissue sample therebetween. The forceps device is then removed from the guide sheath so that the captured tissue may be examined. In practice, physicians have found some difficulty in operating the forceps device such as when attempting to exert sufficient force to remove the forceps device and the captured tissue from the body vessel. This could be alleviated if the handle assembly be modified such that it could pivot or rotate at an angle relative to the patient's body vessel to provide sufficient room for the physician to grasp the handle assembly and then remove the forceps from the body vessel.

SUMMARY OF THE INVENTION

In accordance with the present invention there is provided an improved biopsy forceps device having a handle assembly including a handle portion having a distal end and a hub portion connected to the distal end of the handle portion. An elongated flexible hollow body portion, such as a coiled spring guide wire, is provided having a lumen extending therethrough. A forceps assembly is coupled to the distal end of the body portion with the assembly including a pair of forceps. The hub portion has a lumen extending therethrough and is coupled between the handle portion and the proximal end of the body portion. A control wire extends through the lumen in the body portion and through the lumen in the hub portion and is coupled at one end to the handle portion and the other end to the forceps assembly. A flexible coupling interconnects one end of the hub portion with the distal end of the handle portion so that the hub portion may be angularly displaced with respect to the distal end of the handle portion. More specifically the flexible coupling takes the form of a ball and socket arrangement, including a ball member and a socket member with one of the members being carried by the handle portion and the other member being carried by the hub portion. This permits a physician to angularly displace the handle portion away from the patient's body when exerting force to remove the forceps and captured tissue from the patient.

In accordance with a still further aspect of the present invention the ball member is carried by the hub portion and the socket member is carried by the handle portion. The ball member has a passageway extending therethrough in communication with a lumen extending through the hub portion so that the control wire means may extend through the lumen in the ball member and coupled at one end to the handle portion and at the other end to the forceps assembly.

DESCRIPTION OF THE DRAWINGS

The foregoing and other objects of the invention will become more readily apparent from the following description of the preferred embodiment of the invention as taken in conjunction with the accompanying drawings which are a part hereof wherein:

FIG. 1 is a perspective view of a biopsy forceps device constructed in accordance with the present invention;

FIG. 2 is a sectional view taken along line 2—2 looking in the direction of the arrows in FIG. 1;

FIG. 3 is an enlarged view of a portion of the length of that illustrated in FIG. 2; and FIG. 4 is an enlarged view of a portion shown in FIG. 3 but rotated 90 degrees.

DESCRIPTION OF THE PREFERRED EMBODIMENTS

Reference is now made to the drawings wherein the drawings are for purposes of illustrating a preferred embodiment only and not for purposes of limiting same. As shown in the drawings there is provided a biopsy forceps device 10 which includes a handle assembly 12 which includes a handle portion 14 and a hub portion 16 having its proximal end connected to the distal end of the handle portion 14 by means of a flexible coupling 18, to be described in greater detail hereinafter. In addition to the handle assembly 12 the forceps device 10 includes an elongated flexible hollow body taking the form of a coil spring guide wire 20 which extends from the distal end 22 of hub portion 16 to a forceps assembly 24. The guide wire 20 has a lumen extending throughout its length and slidably receives a control wire 26 which connects at its distal end to the forceps assembly 24 and at its proximal end extends through hub portion 22, the flexible coupling 18 and then into the handle portion 14.

The handle assembly 14 includes a thumb receiving end ring 30 and a FIG. 8 shaped trigger 32. Trigger 32 has a hollow middle portion 34 slidably received over and on the handle portion 14 and opposed finger rings 36 and 38.

As best shown in FIGS. 1 and 2 the handle portion 14 has a lonqitudinally extending transverse slot 40 therethrough in which there is positioned a spring 42 which extends between a forward wall 44 of the slot 40 and a plug member 46 connected to the trigger 32. Connected to the plug member 46 is a proximal end 50 of the control wire 26. Specifically, the proximal end 50 of the control wire 26 is received in a bore of the plug member 46 which also has a transverse bore therein which receives a pin 52. The pin 52 extends through the middle portion 34 of the trigger 32 as well as through the plug member 46. The proximal end 50 of the wire 26 extends through a transverse passageway in the pin 52 and is anchored to the proximal end of the plug member 46. The distal end of the plug member 46 has its diameter reduced somewhat so as to receive a portion of the length of the coil spring 42 with the neck down portion of the plug member serving as a stop to hold the spring in place. The spring 42 resiliently urges the trigger member to the position as shown in FIGS. 1 and 2.

The control wire extends from the distal end of plug member 46 and then through the lumen in the coil spring 42 and then through a passageway 56 in the handle portion 14. The control wire extends through a lumen in the flexible coupling 18, to be described in greater detail hereinafter, and then through a lumen 62 in the hub portion 16.

The hub portion 16 has a proximal end 64 and an inwardly tapering conical shaped distal end 22. The control wire 26 extends through the lumen 62 of the hub member 16 and exits from the distal end of the hub member and then extends through a lumen in the coil spring guide wire 20 to the forceps assembly 24.

The proximal end of the coil spring guide wire 20 extends within the lumen 62 in the hub member 16 for a short distance and is held in place as with a press fit. The coil spring guide wire 20, containing the control wire, then extends for a length on the order of three feet to its distal end at which the control wire is connected to a pair of forceps 24.

In operation a physician employing the forceps device may insert a guide sheath into a body vessel, such as an artery, and then insert the control wire including the forceps assembly into the sheath and guide it to a site containing tissue to be captured. The forceps are opened by displacing the finger rings 36 and 38 in a forward direction against the bias of the spring 42 and then pulled rearwardly with the assistance of the spring to close the forceps to capture tissue to be removed from the patient for examination. The structure and operation of the forceps device as described herein but for the flexible coupling 18 is basically the same as that described in the aforesaid U.S. Pat. No. 4,815,476 to J. P. Clossick the disclosure of which is incorporated herein.

The flexible coupling 18 facilitates the physician's use of the biopsy device since the handle portion 14 may be angularly displaced with respect to the hub portion 16 and this facilitates removing a tissue sample when employing sufficient force to the handle portion during the removal process.

In the prior art, such as in the aforesaid U.S. Pat. No. 4,815,476 to J. P. Clossick, the control wire extending from the handle assembly to the forceps assembly is a length of solid metal. The use of such a wire extending through the flexible coupling of the present invention may well result in the wire taking on a permanent bend when the handle portion 14 is bent at a sever angle relative to the hub portion 16.

In the present invention, the control wire 26 includes a length of flexible stranded wire 70 which extends through the handle portion 14 and through the hub portion 16 and extends beyond the hub portion within the surrounding coiled spring guide wire 20. Forwardly of the distal end 22 of the hub portion the stranded wire 70 is connected to a length of solid wire 72 which then extends in a conventional manner to the distal end of the control guide wire 20 and is coupled to the forceps assembly 24. The stranded wire 70 and the solid wire 72 may be interconnected, as by welding. As shown in FIG. 4 a metal sleeve surrounds a portion of the lengths of the two wires at their abutting ends and the sleeve 74 is crimped to hold the abutting ends together and is welded or soldered to the two wires. This construction preserves the use of the solid control wire extending throughout essentially the entire length of the coil spring guide wire 20 while using a flexible strand of wire within the handle assembly and particularly through the flexible coupling so that bending thereof will not result in the flexible strand of wire taking on a permanent bend.

The flexible coupling 18 includes a ball and socket arrangement which may be constructed of plastic parts. This arrangement includes a ball 80 having a radially extending tube 82 having a lumen therein which communicates with a passageway 84 extending through the ball with the passageway and the lumen being of sufficient size to slidably receive the stranded wire 70 therethrough. The tube 82 extends into the lumen 62 within the hub portion 16 and is held there in place as with a press fit. The socket is formed on the distal end of an end cap 90 which is threaded onto the distal end 58 of the handle assembly 14. The tip of the distal end 58 has a semi-spherical indented surface which serves as a bearing seat 92 for the spherical surface of ball 80 during operation. The distal end of the end cap 90 has a circular opening 94 which is of smaller diameter than that of the ball 80 so that the ball is held in place within the end cap up against the bearing seat 92. The circular hole 94 is surrounded by four socket portions 96 each having an inner face against which the ball 80 seats against. These socket portions 96 are each separated by a longitudinally extending slot 98 having a width slightly greater than that of the outer diameter of tube 82. These slots are located at 0 degrees, 90 degrees, 180 degrees and 270 degrees as viewed from the bottom of the end cap and as is illustrated in FIG. 1. This permits pivotal movement of the ball in two mutually perpendicular planes with a pivotal movement on the order of greater than 60 degrees but less than 90 degrees with the tube being selectively positioned at either 0 degrees, 90 degrees, 180 degrees or 270 degrees. The end cap 90 may be threaded onto the distal end 58 of the handle assembly to adjust the amount of friction between the ball and the bearing seat 92 as desired by the physician. Thus, if there is too much friction the end cap may be loosened to relieve the friction and conversely if there is too little friction the end cap may be tightened. In this way, a means is provided for adjusting the friction between the ball and the ball seat 92 as well as being the ball and the surrounding socket portions 96.

Although the invention has been described in conjunction with a preferred embodiment it is to be understood that various modifications may be made without the parting of the spirit and scope of the invention as defined by the appended claims.

I claim:

1. A biopsy forceps device comprising:
   a handle assembly including a handle portion having a proximal end and a distal end and a hub portion;

an elongated flexible hollow body portion having a lumen extending therethrough and having a proximal end and a distal end;

a forceps assembly coupled to the distal end of said body portion and including a pair of forceps;

said hub portion having a lumen extending therethrough, said hub portion being coupled between said handle portion and the proximal end of said body portion;

trigger means slidably carried by said handle portion for slidable movement between said handle portion's proximal and distal ends;

control wire means extending through the lumen in said body portion and the lumen in said hub portion and coupled at one end to said trigger means and at the other end to said forceps assembly; and flexible coupling means including a ball and socket arrangement interconnecting said hub portion with the distal end of said handle portion and including a ball member and a socket member with one of said members being carried by said handle portion and the other of said members being carried by said hub portion permitting relative angular movement between said hub portion and said handle portion in a plurality of mutually perpendicular planes and wherein said ball member has a lumen extending therethrough, said control wire means extending through and beyond said ball member lumen to said trigger means.

2. A biopsy forceps device as set forth in claim 1 wherein said ball member is carried by said hub portion and said socket member is carried by said handle portion.

3. A biopsy forceps device as set forth in claim 2 wherein said socket member includes wall portions that exert friction on said ball member as it is angularly displace within said socket member.

4. A biopsy forceps device as set forth in claim 3 including means for angularly adjusting the amount of friction applied by said socket member wall portions to said ball member.

5. A biopsy forceps device as set forth in claim 4 wherein said socket member includes an end cap threadably secured to the distal end of said handle assembly.

6. A biopsy forceps device as set forth in claim 5 wherein said ball member has a tube extending therefrom and said end cap has a circular opening therein of smaller diameter than that of said ball member and through which said tube extending from said ball member extends.

7. A biopsy forceps device as set forth in claim 6 wherein said end cap has an annular array of slots formed in its distal end, each slot being of sufficient width to receive a portion of the length of said tube extending from said ball member as said ball member is rotated within said socket member.

8. A biopsy forceps device as set forth in claim 1 wherein said control wire means includes an elongated flexible stranded wire portion and an elongated solid wire portion connected together with said stranded wire portion extending through the lumen in said ball member while said solid wire portion extends through said hollow body portion.

9. A biopsy forceps device as set forth in claim 8 wherein said stranded wire portion is more flexible than said solid wire portion.

10. A biopsy forceps device as set forth in claim 9 wherein one end of said stranded wire portion abuts one end of said solid wire portion and means securing said abutting ends together.

* * * * *

UNITED STATES PATENT AND TRADEMARK OFFICE
CERTIFICATE OF CORRECTION

PATENT NO. : 5,100,430

DATED : March 31, 1992

INVENTOR(S) : Ernesto Avellanet and Ernesto Hernandez

It is certified that error appears in the above-identified patent and that said Letters Patent is hereby corrected as shown below:

Column 6, Line 2, Claim 3, change "displace" to --displaced--.

Column 6, Line 4, Claim 4, delete "angularly".

Signed and Sealed this

Eighth Day of June, 1993

Attest:

MICHAEL K. KIRK

Attesting Officer

Acting Commissioner of Patents and Trademarks